(12) United States Patent
Seguin

(10) Patent No.: US 8,993,611 B2
(45) Date of Patent: Mar. 31, 2015

(54) FAMILY OF POLYAMINE ARYLETHYLAMIDE COMPOUNDS, AND THEIR COSMETIC OR DERMOCOSMETIC USE

(71) Applicant: Exsymol, Monaco (MC)

(72) Inventor: Marie-Christine Seguin, Monaco (MC)

(73) Assignee: Exsymol, Monaco (MC)

( * ) Notice: Subject to any disclaimer, the term of this patent is extended or adjusted under 35 U.S.C. 154(b) by 0 days.

(21) Appl. No.: 13/932,729

(22) Filed: Jul. 1, 2013

(65) Prior Publication Data

US 2014/0005244 A1 Jan. 2, 2014

(30) Foreign Application Priority Data

Jul. 2, 2012 (FR) ...................................... 12 56310

(51) Int. Cl.
*C07D 233/64* (2006.01)
*A61K 31/417* (2006.01)
*A61K 8/49* (2006.01)
*A61Q 19/08* (2006.01)
*C07D 209/14* (2006.01)
*C07C 237/08* (2006.01)

(52) U.S. Cl.
CPC ............ *C07D 233/64* (2013.01); *A61K 31/417* (2013.01); *A61K 8/492* (2013.01); *A61K 8/4946* (2013.01); *A61Q 19/08* (2013.01); *C07D 209/14* (2013.01); *C07C 237/08* (2013.01)
USPC ...................... 514/400; 548/338.1; 548/335.1; 548/494; 564/167; 544/106

(58) Field of Classification Search
USPC ................................. 548/335.1, 494; 564/167
See application file for complete search history.

(56) References Cited

U.S. PATENT DOCUMENTS

| | | | |
|---|---|---|---|
| 6,046,340 A | 4/2000 | Seguin et al. | |
| 7,005,148 B2 | 2/2006 | Pageon | |
| 7,094,796 B2 * | 8/2006 | Seguin ........................ | 514/397 |
| 8,293,294 B2 | 10/2012 | Courtin | |

FOREIGN PATENT DOCUMENTS

| | | |
|---|---|---|
| FR | 2802425 | 6/2001 |
| FR | 2833165 | 6/2003 |
| WO | WO 95/12581 | 5/1995 |
| WO | WO 2010/010248 | 1/2010 |

OTHER PUBLICATIONS

Koroleva, et al. "Artificial Ribonucleases: Quantitative Analysis of the Structure-Activity Relationship and a New Insight into the Strategy of Design of Highly Efficient RNase Mimetics" Russian J. Bioorg. Chem. (2008), 34(4), 442-452.*

King et al. "Primary Amino Acid Derivatives: Compounds with Anticonvulsant and Neuropathic Pain Protection Activities" J. Med. Chem. 2011, 54, 4815.*

Uribarri et al.: "Circulating Glycotoxins and Dietary Advanced Glycation Endproducts: Two Links to Inflammatory Response, Oxidative Stress, and Aging"; J Gerontol A Biol Sci Med Sci. Apr. 2007; vol. 62(4): pp. 427-433.

Dyer et al.: "Accumulation of Maillard Reaction Products in Skin Collagen in Diabetes and Aging"; J. Clin. Invest., vol. 91, Jun. 1993, pp. 2463-2469.

Odetti et al.: "Glycotoxins: a possible treat to health?"; Mediterr J. Nutr. Metab. (2008), vol. 1, pp. 63-67.

Koschinsky et al.: "Orally absorbed reactive glycation products (glycotoxins): An environmental risk factor in diabetic nephropathy"; Proc. Natl. Acad. Sci. USA, vol. 94, Jun. 1997, pp. 6474-6479.

Ogata et al.: "Advanced Glycation Endproducts Act as an Initiator of Skin Tumors in Mice"; Original Article, J. Clin. Biochem. Nutr. vol. 38, May 2006, pp. 176-179.

Ueno et al.: "Characteristics of mutagenesis by glyoxal in *Salmonella typhimurium*: contribution of singlet oxygen"; Mutation Research, vol. 251 (1991), pp. 99-107.

Ahmad et al.: "Genotoxicity and immunogenicity of DNA-advanced glycation end products formed by methylglyoxal and lysine n presence of $Cu^{2+}$"; Biochemical and Biophysical Research Communications, vol. 407 (2011), pp. 568-574.

Wuenschell et al.: "Mutagenic Potential of DNA Glycation: Miscoding by (R)- and (S)- $N^2$-(1-Carboxyethyl)-2'-deoxyguanosine"; Biochemistry, vol. 49 (2010), pp. 1814-1821.

Matsuki et al.: "Metformin restores impaired HDL-mediated cholesterol efflux due to glycation"; Atherosclerosis, vol. 206 (2009), pp. 434-438.

Ulrich et al.: "Pharmacological reversal of advanced glycation end-product-mediated protein crosslinking"; Diabetologia, vol. 40 (1997), pp. S157-S159.

Gugliucchi et al.: "The polyamines spermine and spermidine protect proteins from structural and functional damage by AGE precursors: a new role for old molecules?"; Life Sciences, vol. 72 (2003), pp. 2603-2616.

Roberts et al.: "DNA damage by carbonyl stress in human skin cells"; Mutation Research, vol. 522 (2003), pp. 45-56.

* cited by examiner

*Primary Examiner* — Joseph Kosack
*Assistant Examiner* — Amanda L Aguirre
(74) *Attorney, Agent, or Firm* — Hamre, Schumann, Mueller & Larson, P.C.

(57) ABSTRACT

The invention relates to a family of stable polyamine arylethylamide compounds, and to the use of these compounds as agents inhibiting DNA damages induced by by-products of the non-enzymatic glycosylation of skin tissues.

The invention also relates to cosmetic or dermocosmetic compositions intended to fight skin disorders associated with said glycosylation by-products.

22 Claims, No Drawings

FAMILY OF POLYAMINE ARYLETHYLAMIDE COMPOUNDS, AND THEIR COSMETIC OR DERMOCOSMETIC USE

FIELD OF THE INVENTION

The invention has for object a family of stable polyamine arylethylamide compounds, and the use of these compounds as inhibition agents against DNA damages induced by by-products of skin tissue non-enzymatic glycosylation.

The invention also concerns cosmetic or dermocosmetic compositions intended to fight against skin disorders associated with these same glycosylation by-products.

BACKGROUND OF THE INVENTION

Protein non-enzymatic glycosylation process is a phenomenon identified for a long time, consisting initially in the spontaneous condensation of reducing sugars like glucose or fructose, with the N-terminal amino functions of some protein or lipoprotein constituents like lysine and arginine aminoacids. Contrarily to enzymatic glycosylation process which is genetically programmed, such a process adversely leads to irreversible changes of proteins after a result of chain reactions and of complex molecular rearrangements.

The disturbance of these changes on biological tissues and their cell components is clearly established with multiple physiological consequences: protein functional changes leading to cell metabolism dysfunctions (enzymatic activity disruptions), mechanical property changes of some support tissues, activation of inflammatory processes or of oxidative stress with production of cytokines or of oxygen reactive species, repair process impairments, etc. It is besides evidenced that such changes in proteins play an essential role in the development or speed of some pathologies notably linked to ageing, like sugar diabetes, atherosclerosis, Alzheimer and Parkinson diseases, renal failure, etc. (J. Uribarri et al., J. Gerontol. In Biol. Sci. Med. Sci. (2007), vol. 62, pp. 437-433).

Specifically as far as skin is concerned, the impact of proteins' non-enzymatic glycosylation process, in particular on aging, is undisputed. Indeed once glycated by spontaneous condensation of sugar, skin proteins and in particular those of structures such as collagen or elastin, become rigid with the accumulation of interfibre covalent cross-links. Skin viscoelastic properties are thus reduced, which increases the first signs of emerging wrinkles or already formed wrinkles. The renewal of these skin proteins is also slowed down (Dyer D.G. et al., J. Clinical Invest. (1993), vol.91, pp. 2463-9).

Another well admitted knowledge today, but not least, on protein non-enzymatic glycosylation process is that this complex process also releases some substances often referred to as "glycosylation by-products" that behave like real toxins. Besides like a recent article entitled "*Glycotoxins : a possible threat to health?*" (Odetti P. et al., Mediterr. J. Nutr. Metab., (2008), vol. 1, pp. 63-67), the more suggestive terminology of "glycotoxins" is more and more reported in the literature for designating the whole of deleterious products resulting from the protein non-enzymatic glycosylation process (Koschinski T. et al., Proc Natl. Acad. Sci. USA (1997), vol. 94, pp. 6474-6479). This refers to various substances poorly defined among which compounds such as glyoxal, methyl-glyoxal or deoxyglucosone can be however featured.

A characteristic of glycotoxins especially harmful to living organisms is their ability to damage cellular DNA. Indeed, such alterations can induce gene mutations responsible for a genomic instability. For example, the mutagenicity of by-products, formed when protein bovine albumin (BSA) is in vitro incubated with glucose, has been reported (Ogata M. et al., J. Clinical Biochem. Nutr.(2006) vol. 38, pp. 176-179). Several alpha-ketoaldehydes, especially the aforementioned glyoxal and methyl-glyoxal, are able to induce mutations on genes of bacterial strain and of human cells (Ueno H. et al., Mutation Res. (1991), vol. 251, pp.99-107). More recently, the genotoxic potential of glycotoxins which are likely to result from the formation of stable adducts by reaction with some DNA constitutive nucleosides, has been reported (Ahmad S., Biochem. Biophys. Res. Common. (2011), vol. 15, pp.568-74). Methyl-glyoxal thus targets particularly guanosines from DNA's nucleoside chains, hence leading to the apparition of mutations during the DNA replication process, especially in the absence of an efficient repair (Wuenschell G.E. et al., Biochemistry (2010), vol.49, pp.1814-1821).

Consequently with regard to these different statements, the applicant focused on the identification of substances, with cosmetic or dermocosmetic purpose, able to interfere with protein non-enzymatic glycosylation process with main objective to avoid any damage affecting skin cells' DNA and resulting from glycotoxin production. It is indeed currently of interest in the cosmetic industry, particularly to prevent from skin cells' premature senescence, to protect genomic DNA of cells such as keratinocytes or fibroblasts.

With this objective, the applicant more precisely searched for original structures able to trap glycosylation by-products during the protein non-enzymatic glycosylation process, like the above-described genotoxic glycotoxins, while caring about that the formed adducts (glycotoxin-trapper) are not genotoxic, but also preventing these same adducts from leading to the formation of products themselves genotoxic. It is effectively of first importance in the frame of a cosmetic or dermocosmetic purpose, besides the innocuousness of substances, also to make sure of the innocuousness of reaction by-products resulting from the targeted cosmetic activity.

Concerning the state of the art attached to the applicant's objectives, the prior art essentially reveals, to the knowledge of the applicant, substances or preparations which display a simple preventive or inhibiting profile in the glycosylation products' formation. Thus, for example, the guanidine family substances such as aminoguanidine and metformin are of therapeutic interest for their ability to bind early glycosylation by-products (Matsuki K. et al., Atherosclerosis (2009), vol. 206, pp. 434-8). Several salts of thiazolium, especially N-phenacyl thiazolium bromide or "PTB", would also be of therapeutic interest thanks to their ability to break the crossed links between proteins (Ulrich P. et al., Diabetologia (1997), vol. 40, pp. S157-S159).

In regard to skin care, some benzofuran hydroxylated derivatives are used in cosmetic purposes for their restricting properties, even disclosed as inhibiting properties, towards the non-enzymatic glycosylation reaction of dermal or keratinic proteins (patent FR 2833165). The applicants of patents FR 2802425 and WO 2010/010248 succeeded in identifying plant extracts, respectively of Ericaceae and Sapotaceae families, for skin cell and protein protection with a same restricting or inhibiting result. But it has to be underlined that none of these documents provides in combination, information about a benefit to skin cells' DNA when specifically subjected to genotoxic glycotoxins, and information about the becoming of detoxified glycosylation by-products. More broadly, the antioxidant qualities of products with an imidazole group are also mentioned in patent application WO95/12581 filed by the applicant, these compounds being used for various therapeutic and cosmetological applications.

BRIEF SUMMARY OF THE INVENTION

With as initial basis to aim at a linear polyamine structure like spermine and spermidine substances of interest against the non-enzymatic glycosylation of some proteins (Gugliucci A. et al. Life Sciences (2003), vol.72, pp.2603-2616), the applicant thus discovered that a reduced family of compounds, obtained by coupling reaction between a panel of aminoalkanoic acids and primary ethylamines bearing an aromatic ring or an aromatic heterocycle, revealed a general behaviour of inhibitor of DNA damages induced by deleterious glycosylation by-products such as glycotoxins. The compounds of the invention, represented by formulae (I), (II) and (III) below, display the following advantageous properties:

- an ability to protect a target nuclear protein favoured of glycotoxins, histones [see test 1 below]. Histones constitute essential proteins to DNA packing around nucleosome, since they orchestrate the level of compaction or relaxation of chromatin that is the form under which DNA is presented in the nucleus and that enables an accessibility of repair systems to the damage site of DNA (Roberts et al., Mutation Res. (2003), vol.522, pp.45-56);
- an ability to delete mutagenicity of genotoxic by-products from the non-enzymatic glycosylation of a protein by fructose, reflected by an ability to reduce significantly and even totally the number of mutations (so-called "reverses") induced in a reference prokaryote [see test 2 below];
- an ability to delete mutagenicity of a reference glycotoxin, methyl-glyoxal [see test 3 below];
- an ability to interfere with the non-enzymatic glycosylation process with the property not to form, under glycosylating conditions, genotoxic by-products, or not to evolve under these conditions towards the formation of such by-products [see test 4 below].

DETAILED DESCRIPTION OF THE INVENTION

The invention has therefore for first object a family of polyamine arylethylamide compounds, characterized in that said family is represented by the following general formula (I):

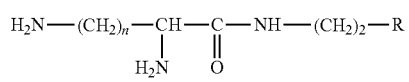
(I)

wherein: n=1 to 4
and

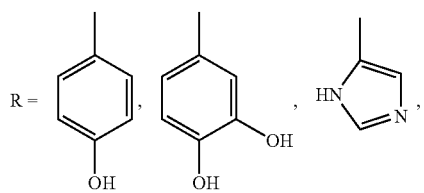

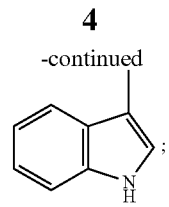

with the exception of the compound where n=3 and R=imidazole.

According to a preferred embodiment of the invention, the compounds according to the invention are represented by the following formula (II):

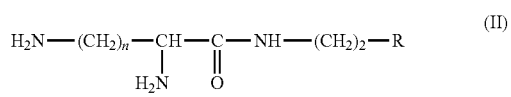
(II)

wherein: n=1 to 2
and

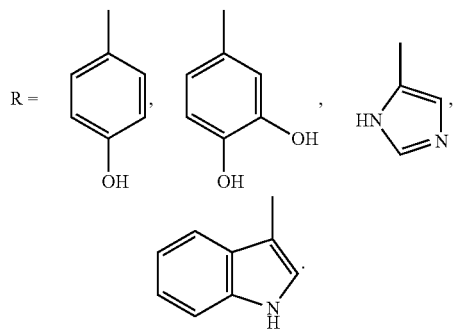

According to another preferred embodiment of the invention, the compounds according to the invention are represented by the following formula (III):

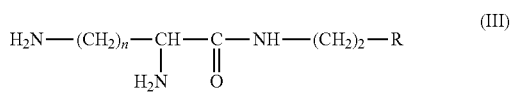
(III)

wherein n=1 to 2
and

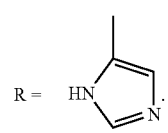

In one aspect, the invention is also directed to pharmaceutically acceptable salts of the compounds of formula (I), (II) or (III).

As non exhaustive examples of polyamine arylethylamide compounds with formula (I), the following compounds can be mentioned:
N-((4-imidazolyl)ethyl)-L-lysinamide
N-((4-imidazolyl)ethyl)-α,γ-diaminobutanamide
N-((4-imidazolyl)ethyl)-α,β-diaminopropanamide
N-((3-indolyl)ethyl)-α,β-diaminopropanamide N-((4-hydroxyphenyl)ethyl)-α,β-diaminopropanamide
N-((3,4-dihydroxyphenyl)ethyl)-α,β-diaminopropanamide As non exhaustive examples of polyamine arylethylamide compounds with formula (II), the following compounds can be mentioned:
N-((4-imidazolyl)ethyl)-α,γ-diaminobutanamide
N-((4-imidazolyl)ethyl)-α,β-diaminopropanamide
N-((3-indolyl)ethyl)-α,β-diaminopropanamide
N-((4-hydroxyphenyl)ethyl)-αβ-diaminopropanamide
N-((3,4-dihydroxyphenyl)ethyl)-α,β-diaminopropanamide The polyamine arylethylamide compounds with formula (III) are the following:
N-((4-imidazolyl)ethyl)-α,γ-diaminobutanamide
N-((4-imidazolyl)ethyl)α,β-diaminopropanamide According to a more advantageous embodiment of the invention, the aforementioned formulae (I), (II) and (III) very specifically target N-((4-imidazolyl)ethyl)-α,β-diaminopropanamide and N-((4-imidazolyl)ethyl)-α,γ-diaminobutanamide as polyamine arylethylamide compounds.

The compounds of the invention can be synthesized according to methods which are known by the skilled person, for example according to common chemical approaches to peptide synthesis (protection, coupling and deprotection sequences). Salts of the compounds of the invention can be obtained by reaction of the compounds with an inorganic acid (e.g. hydrochloric acid, hydrobromic acid, sulphuric acid, phosphoric acid) or an organic acid (e.g. fumaric acid, maleic acid, oxalic acid, citric acid, trifluoroacetic acid, tartaric acid, a sulfonic acid—from methanesulfonic acid to dodecanesulfonic acid).

According to another aspect, the invention also covers a composition, for cosmetic or dermocosmetic use, intended to prevent or to limit the "genotoxic risk" associated to the non-enzymatic glycosylation process, and in particular associated to the formation of genotoxic glycosylation by-products (glycotoxins).

Said composition comprises in association with any physiologically acceptable additive with skin, as main active ingredient, a compound of general formulas (I), (II) and (III) such as here-above defined. It is presented in powdery solid form, soluble in aqueous or hydroalcoholic medium but insoluble in ethanol, stable on a great range of pH (3-9).

In the course of the present invention, it is understood by "main active ingredient" an active substance able to detoxify glycotoxins and to oppose their formation and deleterious effects.

Advantageously, the amount of compound of general formula (I) in the here-above composition is comprised between 0.01% and 1% in weight in relation to the total weight of the composition, preferably between 0.01% and 0.5% in weight, more even particularly between 0.02% and 0.2% in weight.

The compositions according to the invention are adapted to a cutaneous topical administration presented under all forms normally used for such an administration. As indicative but not restrictive examples, compositions can be presented under the form of emulsions, lotions, creams, aqueous or hydroalcoholic gels, powders, and various emulsions that can be possibly microemulsions or nanoemulsions, etc.

The compositions according to the invention can also be formulated for an administration by oral route exemplified without restriction by a tablet, a capsule, a capsule, a pill, a pouch, a paste, a liquid (emulsified or not).

The compositions according to the invention can contain as physiologically acceptable additive at least one additive known by the skilled person and compatible in cosmetic or dermocosmetic areas, chosen among oils, waxes, silicone elastomers, surfactants, co-surfactants, thickeners and/or gellants, humectants, emollients, organic or inorganic filters, photostabilizing agents, preservatives with the exception of aldehyde donor preservatives, dyes, matifying agents, tensors, sequestering agents, perfumes, etc., and their mixtures.

The compositions according to the invention can also comprise one or several additional active ingredients, the skilled person ensuring however that the possible active supplements as well as their proportions are chosen in such a way that advantageous properties recognized to the compositions according to the invention are not affected. These additional active ingredients can be chosen, without the list being limited, among deglycation agents, agents that increase the synthesis of collagen or elastin or prevent their degradation, agents that increase the synthesis of glycosaminoglycans or proteoglycans or prevent their degradation, agents that increase the cell proliferation, depigmenting or pro-pigmenting agents, antioxidant or anti-radical or anti-pollution agents, moisturizer agents, agents that stimulate lipolysis, draining or detoxifying agents, anti-inflammatory agents, penetration enhancer agents, desquamative agents, soothing and/or anti-irritating agents, astringent agents, agents that act on the microcirculation, etc., and their mixtures.

The compositions according to the invention aim at preventing or at fighting any skin disorders associated with the protein non-enzymatic glycosylation process and to the genotoxic glycotoxin formation, chosen among premature senescence of skin cells, skin lightening, etc. In such compositions, the polyamine arylethylamide compound is preferentially of formula (III), more particularly the N-((4-imidazolyl)ethyl)-α, β-diaminopropanamide compound.

Another object of the invention concerns the cosmetic or dermocosmetic use of a polyamine arylethylamide compound as inhibiting agent of DNA damages induced by genotoxic glycotoxins, said polyamine arylethylamide compound being of following general formula (I):

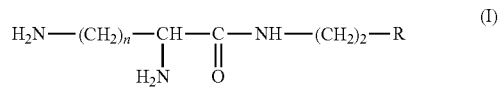

wherein: n=1 to 4
and

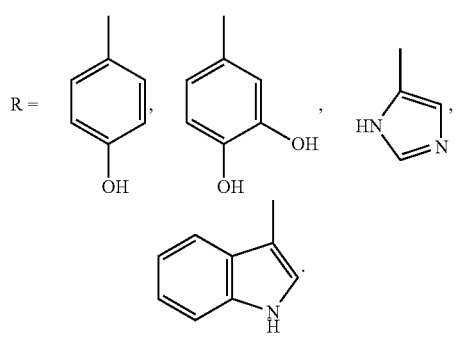

Preferably within the above use, a compound of formula (III) is selected:

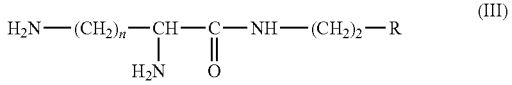

wherein: n=1 to 2
and

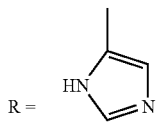

and preferably the N-((4-imidazolyl)ethyl)-α,β-diaminopropanamide compound.

Another object of the invention concerns a cosmetic care method that comprises the application of a cosmetic composition such as previously defined on at least a skin part of body, according to an efficient amount to fight against skin disorders associated to the non-enzymatic glycosylation by-products of skin tissues.

EXAMPLES

Example 1

For illustrative purposes, two formulation examples of composition according to the invention are mentioned hereafter, with a polyamine arylethylamide compound of above general formula (I):

| Formula A (cream) | |
|---|---|
| N-((4-imidazolyl)ethyl)-α,β-diaminopropanamide | 0.05% |
| Hydrogenated polyisobutene | 7% |
| Isobutyl myristate | 3% |
| Cetyl Palmitate | 7% |
| Ethylene glycol monostearate | 5% |
| Sorbitan laurate | 2% |
| Polysorbate 20 | 2% |
| Carbomer (acrylate copolymer/acrylamide & mineral oil) | 0.3% |
| Phenoxyethanol | 0.5% |
| Water | qsp 100% |

| Formula B (gel) | |
|---|---|
| N-((4-imidazolyl)ethyl)-α,γ-diaminobutanamide | 0.1% |
| Carbomer (acrylate copolymer/acrylamide & mineral oil) | 1.5% |
| Sodium benzoate | 0.2% |
| Sorbic acid | 1% |
| 1,3-butanediol | 10% |
| Glycerin | 5% |
| Sodium carbonate | 0.13% |
| Phenoxyethanol | 0.9% |
| Water | qsp 100% |

Example 2

Merely by way of information, the invention is hereafter illustrated by the following tests which are above-mentioned in the description of the invention (tests 1 to 4).

It is also to be noted that the first results of in vivo studies achieved in humans (repeated application test under patch, provider: Evic Romania Company) underline a good skin tolerance of a polyamine arylethylamide compound according to the present invention.

Test 1: Evidence of the Ability of the polyamine arylethylamide Compounds of General Formula (I) to Protect some Proteins Essential to Nuclear DNA Packing, Histones, Towards a Reference glycotoxin, methyl-glyoxal (MGO)

A solution of purified histones (5 mg/l), enriched with H1 histones, was incubated in the presence of the reference glycotoxin MGO (10 mM) during 24 h at 37° C. under stirring. In order to follow specifically fluorescence of products from non-enzymatic glycosylation of histones, it was necessary to get rid of MGO fluorescence as well as the one of the glycotoxin-trapper products. For this, the reaction mixture was dialyzed. Then it was introduced in a dialysis tape and three successive 3 hour-baths were run, each one in a $NaH_2PO_4$ buffer solution (83.3 mM) in which MGO was diluted. Dialyzed mixture fluorescence which was indicative of the damage of histones made by reaction with MGO (adduct formation) was measured by fluorimetry (λ excitation: 340 nm; λ emission: 470 nm). The measure unit corresponds to RFU (for "Relative Fluorescence Unit").

TABLE 1

| Compound | RFU |
|---|---|
| histones + MGO 10 mM (control) | 62231 |
| N-((4-imidazolyl)ethyl)-α,β-diaminopropanamide 10 mM + histones + MGO 10 mM | 20441 |
| N-((4-imidazolyl)ethyl)-α,γ-diaminobutanamide 10 mM + histones + MGO 10 mM | 21526 |

The results show that the N-((4-imidazolyl)ethyl)-α,β-diaminopropanamide and N-((4-imidazolyl)ethyl)-α,γ-diaminobutanamide compounds according to the invention have the ability to strongly decrease the formation of non-enzymatic glycosylation products resulting from the reaction of glycotoxin with histones.

Test 2: Evidence of the Ability of the polyamine arylethylamide Compounds of General Formula (I) to Detoxify glycotoxins Released by a Glycosylated Protein The study was achieved on a *Salmonella typhimurium* (TA 100) bacterial strain which belongs to reference strains used for the Ames regulatory test (ICH steering committee, Jul. 19, 1995, Guidance on specific aspect of regulatory genotoxicity tests for pharmaceuticals). The objective was to determine, in the mutated strains' colonies, the number of revertant colonies which are representative of mutagenesis in casein-fructose system, with or without a compound according to the invention.

Experimentally, 2.7 g of D-(+)-fructose were solubilized at room temperature in 100 mL of phosphate buffer. After collecting 20 g of the colourless limpid solution ($C_{fructose}$=150 mM), 0.600 g of sodium caseinate were introduced until complete dissolution. The solution was then introduced in 2×10mL in screw-top test tubes, then placed in an oil bath at 120° C. during 1 h.

In parallel, the TA 100 strain was cultured in the Nutrient Broth Oxoid N° 2 (NBO2) supplemented with Ampicilline. The culture was placed overnight at 37° C. in an orbital shaker (88 rpm) so that bacteria were in growth exponential phase ($10^7$ to $10^9$ bacteria/ml). Moreover, 0.92 g of compound according to the invention, N-((4-imidazolyl)ethyl)-α,β-di-amino-propanamide, were solubilized in a freshly prepared solution of phosphate buffered saline (PBS). To different concentrations (400 µl) of compound according to the invention were successively added 500 µl of glycated casein and 100 µl of the above-mentioned bacterial suspension. The resulting mixture was incubated 30 minutes at 37° C. under orbital stirring (122 rpm). 2 ml of soft-agar supplemented in biotin histidine and maintained at 45° C. were added. After mixing with Vortex, they were deposited in a Petri dish containing Vogel-Bonner hard-agar. After solidification, dishes were transferred in the incubator at 37° C. during 48-72 h.

The assay was achieved without metabolic activator according to the pre-incubation method on the TA 100 strain. The counting of colonies was then achieved manually.

The results are presented in table 2 below, compared to a negative control (PBS phosphate buffer).

TABLE 2

| Compound | Number of revertants | RFU |
| --- | --- | --- |
| Control (PBS) | 84 | 1 |
| Fructosylated casein | 138 | 1.64 |
| N-((4-imidazolyl)ethyl)-α,β-diaminopropanamide (7.5 mM) | 119 | 1.42 |
| N-((4-imidazolyl)ethyl)-α,β-diaminopropanamide (15 mM) | 93 | 1.11 |

The results show that the N-((4-imidazolyl)ethyl)-α,β-diaminopropanamide compound according to the invention is able to strongly decrease toxicity of the formed glycotoxins. A dose-effect relationship is furthermore observed.

Test 3: Evidence of the Ability of the polyamine arylethylamide Compounds of General Formula (I) to Detoxify a Reference Glycotoxin, methyl-glyoxal (MGO)

The study was carried out according to an almost-identical manner to the here-above test 2, with however a MGO solution at the concentration of 140 µM replacing the 500 µl of glycated casein. In addition to the N-((4-imidazolyl)ethyl)-α,β-diaminopropanamide compound, the following compounds according to the invention were also tested at different concentrations:

N-((4-hydroxyphenyl)ethyl)-α,β-diaminopropanamide
N-((4-imidazolyl)ethyl)-α,γ-diaminobutanamide
N-((3,4-dihydroxyphenyl)ethyl)-α,β-diaminopropanamide
N-((4-imidazolyl)ethyl)-L-lysinamide The results are gathered in table 3 below, compared to the PBS phosphate buffer (negative control).

TABLE 3

| Compound | Number of revertants |
| --- | --- |
| Control (PBS) | 72 |
| Methyl-glyoxal 280 µM | 308 |
| N-((4-imidazolyl)ethyl)-α,β-diaminopropanamide (75 µM) | 141 |
| N-((4-imidazolyl)ethyl)-α,β-diaminopropanamide (750 µM) | 95 |
| Control (PBS) | 91 |
| Methyl-glyoxal 140 µM | 161 |
| N-((4-hydroxyphenyl)ethyl)-α,β-diaminopropanamide (75 µM) | 152 |
| Control (PBS) | 91 |
| Methyl-glyoxal 140 µM | 161 |
| N-((4-imidazolyl)ethyl)-α,γ-diaminobutanamide (75 µM) | 154 |
| N-((4-imidazolyl)ethyl)-α,γ-diaminobutanamide (750 µM) | 116 |
| Control (PBS) | 91 |
| Methyl-glyoxal 140 µM | 161 |
| N-((3,4-dihydroxyphenyl)ethyl)-α,β-diaminopropanamide (75 µM) | 161 |
| N-((3,4-dihydroxyphenyl)ethyl)-α,β-diaminopropanamide (750 µM) | 111 |
| Control (PBS) | 91 |
| Methyl-glyoxal 140 µM | 161 |
| N-((4-imidazolyl)ethyl)-L-lysinamide (75 µM) | 141 |
| N-((4-imidazolyl)ethyl)-L-lysinamide (750 µM) | 132 |

The results show that a fairly broad range of compounds according to the invention are able to strongly reduce the methyl-glyoxal mutagenicity.

Test 4: Evidence of the Ability of the polyamine arylethylamide Compounds of General Formula (I) to Interfere with the Non-Enzymatic Glycosylation Process without the Formation of Mutagenic by-Products The study was carried out according to an almost-identical manner to the here-above test 2, with however D-glucose replacing D-(+)-fructose and according to following conditions. Experimentally, 18.02 g of D-glucose were solubilized at room temperature in 100 mL of water. 10 mL of the solution corresponding to 10 mM of the compound according to the invention, N-((4-imidazolyl)ethyl)-α,β-diamino-propanamide, were sampled and introduced after a pH adjustment by sodium hydroxide. The resulting reaction mixture was then introduced in a screw-top test tube, then heated at 100° C. for 80 minutes.

In parallel, the TA 100 strain was cultured in the Nutrient Broth Oxoid N° 2 (NBO2) supplemented with Ampicilline. The culture was placed overnight at 37° C. in an orbital shaker (88 rpm) so that bacteria were in growth exponential phase ($10^7$ to $10^9$ bacteria/ml).

100 µl of test solution were added to 100 µl of the above-mentioned bacterial suspension and to 500 µl of PBS phosphate buffer, the resulting mixture being incubated 1 h at 37° C. under orbital stirring (122 rpm). 2 ml of soft-agar supplemented in biotin histidine and maintained at 45° C. were added. After mixing with Vortex, they were deposited in a Petri dish containing Vogel-Bonner hard-agar. After solidification, dishes were transferred in the incubator at 37° C. during 48-72 h.

The assay was achieved without metabolic activator according to the pre-incubation method on the TA 100 strain. The counting of colonies was then achieved manually. The results are presented in table 4 below, compared to a negative control (PBS phosphate buffer) and a positive control (sodium azide $NaN_3$).

TABLE 4

| Compound | Number of revertants |
| --- | --- |
| Control (PBS) (spontaneous revertants) | 88 |
| Control ($NaN_3$) (positive control) | 211 |
| N-((4-imidazolyl)ethyl)-α,β-diaminopropanamide (1.667 µl/dish) | 104 |
| N-((4-imidazolyl)ethyl)-α,β-diaminopropanamide (25 µl/dish) | 95 |
| N-((4-imidazolyl)ethyl)-α,β-diaminopropanamide (50 µl/dish) | 90 |
| N-((4-hydroxyphenyl)ethyl)-α,β-diaminopropanamide (50 µl/dish) | 93 |
| N-((4-imidazolyl)ethyl)-α,γ-diaminobutanamide (50 µl/dish) | 93 |
| N-((4-imidazolyl)ethyl)-L-lysinamide (50 µl/dish) | 99 |

The results show that the polyamine arylethylamide compounds of general formula (I) according to the invention do not release mutagenic by-products, despite the glycosylating conditions.

The invention claimed is:

1. A polyamine arylethylamide compound represented by following formula (II):

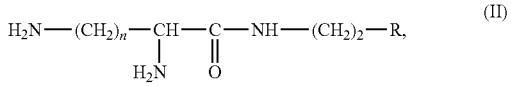

wherein n is 1 or 2, and R is

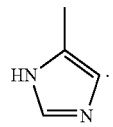

2. The compound according to claim 1, which is N-((4-imidazolyl)ethyl)-α,β-diamino-propanamide.

3. A cosmetic or dermocosmetic composition, which comprises as main active ingredient a compound as defined in claim 1, or a pharmaceutically acceptable salt thereof, and further comprises at least one additive that is physiologically acceptable for skin.

4. The composition according to claim 3, wherein said compound is N-((4-imidazolyl)-ethyl)-α,β-diaminopropanamide.

5. The composition according to claim 3, wherein an amount of said compound in the composition is between 0.01% and 1% by weight relative to a total weight of the composition.

6. The composition according to claim 3, which further comprises one or more additional active ingredients selected from the group consisting of deglycation agents, agents that increase synthesis of collagen or elastin, agents that increase synthesis of glycosaminoglycans or proteoglycans, agents that increase cell proliferation, depigmenting or pro-pigmenting agents, antioxidant or anti-radical or anti-pollution agents, moisturizer agents, agents that stimulate lipolysis, draining or detoxifying agents, anti-inflammatory agents, penetration enhancer agents, desquamative agents, soothing or anti-irritating agents, astringent agents, agents that act on microcirculation, and their mixtures.

7. The compound according to claim 1, which is N-((4-imidazolyl)ethyl)-α,γ-diaminobutanamide.

8. A cosmetic or dermocosmetic composition, which comprises as main active ingredient a compound as defined in claim 7, and further comprises at least one additive that is physiologically acceptable for skin.

9. A polyamine arylethylamide compound represented by following formula (II):

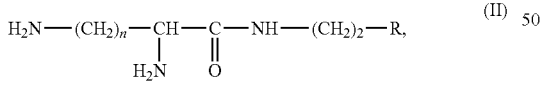

wherein n is 1 or 2, and R is

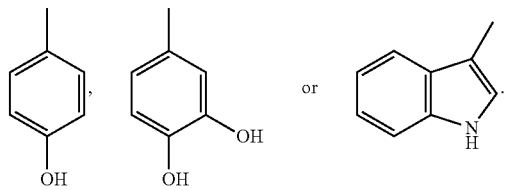

10. A cosmetic or dermocosmetic composition, which comprises as main active ingredient a compound as defined in claim 9, and further comprises at least one additive that is physiologically acceptable for skin.

11. The composition according to claim 10, wherein an amount of the compound of formula (II) in the composition is between 0.01% and 1% by weight relative to total weight of the composition.

12. The composition according to claim 10, which further comprises one or several additional active ingredients selected from the group consisting of deglycation agents, agents that increase the synthesis of collagen or elastin, agents that increase the synthesis of glycosaminoglycans or proteoglycans, agents that increase the cell proliferation, depigmenting or pro-pigmenting agents, antioxidant or anti-radical or anti-pollution agents, moisturizer agents, agents that stimulate lipolysis, draining or detoxifying agents, anti-inflammatory agents, penetration enhancer agents, desquamative agents, soothing or anti-irritating agents, astringent agents, agents that act on the microcirculation, and their mixtures.

13. A method of treating skin disorders associated with formation of non-enzymatic glycosylation by-products or of genotoxic glycotoxins, which comprises administering to a subject in need thereof a compound of following formula (II):

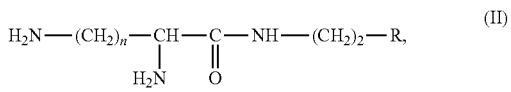

wherein n is 1 or 2, and R is

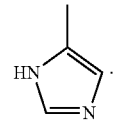

14. The method according claim 13, wherein the skin disorder is premature senescence of skin cells, or skin lightening.

15. The method according to claim 13, wherein said compound is N-((4-imidazolyl)-ethyl)-α,β-diaminopropanamide.

16. A method of inhibiting DNA damages induced by genotoxic glycotoxins, which comprises administering to a subject in need thereof a compound of following formula (II):

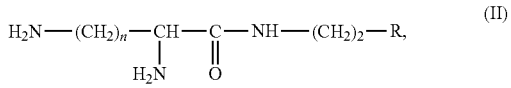

wherein n is 1 or 2, and R is

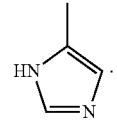

17. The method according to claim 16, wherein said compound is N-((4-imidazolyl)-ethyl)-α,β-diaminopropanamide.

18. A method of opposing mutagenic effects of glycotoxins, which comprises administering to a subject in need thereof a compound of following formula (II):

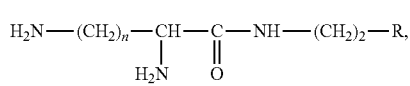

wherein n is 1 or 2, and R is

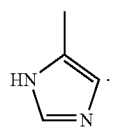

19. The method according to claim 18, wherein said compound is N-((4-imidazolyl)-ethyl)-α,β-diaminopropanarnide.

20. A method of treating skin disorders associated with the formation of non-enzymatic glycosylation by-products or of genotoxic glycotoxins, which comprises administering to a subject in need thereof a compound of following formula (II):

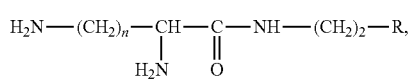

wherein n is 1 or 2, and R is

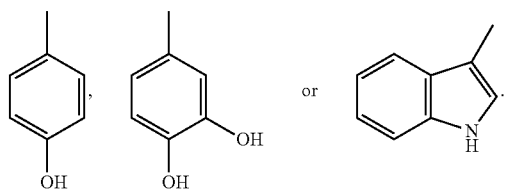

21. A method of inhibiting DNA damages induced by genotoxic glycotoxins, which comprises administering to a subject in need thereof a compound of following formula (II):

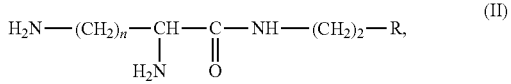

wherein n is 1 or 2, and R is

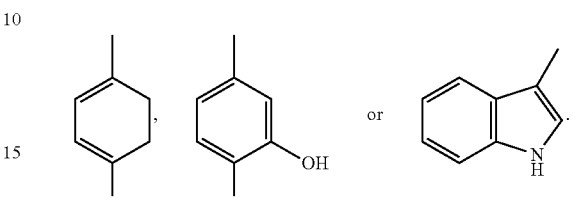

22. A method of opposing the mutagenic effects of glycotoxins, which comprises administering to a subject in need thereof a compound of following formula (II):

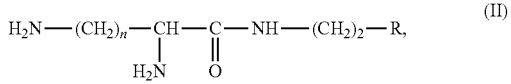

wherein n is 1 or 2, and R is

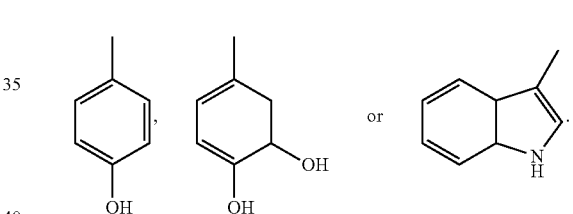

* * * * *